(12) United States Patent
Chen et al.

(10) Patent No.: US 7,091,385 B2
(45) Date of Patent: Aug. 15, 2006

(54) ACYLATION USING MOLECULAR SIEVE SSZ-71

(75) Inventors: Cong-Yan Chen, Kensington, CA (US); Allen W. Burton, Jr., Richmond, CA (US); Ann J. Liang, Davis, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 0 days.

(21) Appl. No.: 11/266,116

(22) Filed: Nov. 2, 2005

(65) Prior Publication Data

US 2006/0142618 A1 Jun. 29, 2006

Related U.S. Application Data

(60) Provisional application No. 60/639,214, filed on Dec. 23, 2004.

(51) Int. Cl.
*C07C 2/66* (2006.01)
*C07C 2/86* (2006.01)
*C07C 45/46* (2006.01)

(52) U.S. Cl. ............. 568/309; 568/319; 568/331; 568/335; 585/467

(58) Field of Classification Search ........... 585/467; 568/309, 319, 331, 335
See application file for complete search history.

(56) References Cited

U.S. PATENT DOCUMENTS

| 3,692,470 | A | * | 9/1972 | Ciric | 423/706 |
| 4,481,174 | A | * | 11/1984 | Baacke et al. | 423/702 |
| 4,623,526 | A | * | 11/1986 | Lam Shang Leen | 423/705 |
| 4,857,288 | A | * | 8/1989 | Marcus et al. | 423/703 |
| 5,399,337 | A | * | 3/1995 | Schmitt | 423/705 |
| 5,653,956 | A | * | 8/1997 | Zones | 423/706 |

* cited by examiner

*Primary Examiner*—David Sample
(74) *Attorney, Agent, or Firm*—Richard J. Sheridan

(57) ABSTRACT

The present invention relates to new molecular sieve SSZ-71 prepared using a N-benzyl-1,4-diazabicyclo[2.2.2]octane cation as a structure-directing agent, methods for synthesizing SSZ-71 and processes employing SSZ-71 in a catalyst.

4 Claims, No Drawings

ACYLATION USING MOLECULAR SIEVE SSZ-71

This application claims the benefit under 35 USC 119 of Provisional Application No. 60/639,214, filed Dec. 23, 2004.

BACKGROUND OF THE INVENTION

1. Field of the Invention

The present invention relates to new molecular sieve SSZ-71, a method for preparing SSZ-71 using a N-benzyl-1,4-diazabicyclo[2.2.2]octane cation as a structure directing agent and the use of SSZ-71 in catalysts for, e.g., hydrocarbon conversion reactions.

2. State of the Art

Because of their unique sieving characteristics, as well as their catalytic properties, crystalline molecular sieves and zeolites are especially useful in applications such as hydrocarbon conversion, gas drying and separation. Although many different crystalline molecular sieves have been disclosed, there is a continuing need for new zeolites with desirable properties for gas separation and drying, hydrocarbon and chemical conversions, and other applications. New zeolites may contain novel internal pore architectures, providing enhanced selectivities in these processes.

Crystalline aluminosilicates are usually prepared from aqueous reaction mixtures containing alkali or alkaline earth metal oxides, silica, and alumina. Crystalline borosilicates are usually prepared under similar reaction conditions except that boron is used in place of aluminum. By varying the synthesis conditions and the composition of the reaction mixture, different zeolites can often be formed.

SUMMARY OF THE INVENTION

The present invention is directed to a family of molecular sieves with unique properties, referred to herein as "molecular sieve SSZ-71" or simply "SSZ-71". Preferably, SSZ-71 is in its silicate, zincosilicate, aluminosilicate, titanosilicate, germanosilicate, vanadosilicate, ferrosilicate or borosilicate form. The term "silicate" refers to a molecular sieve having a high mole ratio of silicon oxide relative to aluminum oxide, preferably a mole ratio greater than 100, including molecular sieves comprised entirely of silicon oxide. As used herein, the term "zincosilicate" refers to a molecular sieve containing both zinc oxide and silicon oxide. The term "aluminosilicate" refers to a molecular sieve containing both aluminum oxide and silicon oxide and the term "borosilicate" refers to a molecular sieve containing oxides of both boron and silicon.

In accordance with the present invention, there is provided a method for performing an acylation reaction on an aromatic substrate $ArH_n$ to form a product $ArH_{n-1}COR$, the method comprising the steps of:
providing the aromatic substrate,
intimately mixing the substrate and an acylating agent, wherein the acylating agent is selected from the group consisting of a carboxylic acid derivative, a carboxylic acid, an acid anhydride, an ester, and an acyl halide, and exposing an intimate mixture thus formed to a catalyst comprising a molecular sieve produced by the method comprising:

(1) preparing an as-synthesized molecular sieve having a composition, as synthesized and in the anhydrous state, in terms of mole ratios as follows:

$YO_2/WO_d$ 15–∞
$M_{2/n}/YO_2$ 0–0.03
$Q/YO_2$ 0.02–0.05 wherein Y is silicon, germanium or a mixture thereof; W is zinc, titanium or mixtures thereof; d is 1 or 2 (i.e., d is 1 when W is divalent or 2 when W is tetravalent); M is an alkali metal cation, alkaline earth metal cation or mixtures thereof; n is the valence of M (i.e., 1 or 2); and Q is a N-benzyl-1,4-diazabicyclo[2.2.2]octane cation, the as-synthesized molecular sieve having the X-ray diffraction lines of Table I;

(2) thermally treating the as-synthesized molecular sieve at a temperature and for a time sufficient to remove the N-benzyl-1,4-diazabicyclo[2.2.2]octane cation from the molecular sieve; and (3) optionally, replacing at least part of the zinc and/or titanium with a metal selected from the group consisting of aluminum, gallium, iron, boron, indium, vanadium and mixtures thereof.

The molecular sieve of the present invention may be predominantly in the hydrogen form, which hydrogen form is prepared by ion exchanging with an acid or with a solution of an ammonium salt followed by a second calcination. If the molecular sieve is synthesized with a high enough ratio of SDA cation to sodium ion, calcination alone may be sufficient. For high catalytic activity, the SSZ-71 molecular sieve may be predominantly in its hydrogen ion form. As used herein, "predominantly in the hydrogen form" means that, after calcination, at least 80% of the cation sites are occupied by hydrogen ions and/or rare earth ions. It should be noted that the mole ratio of the first oxide or mixture of first oxides to the second oxide can be infinity, i.e., there is no second oxide in the molecular sieve. In these cases, the molecular sieve is an all-silica molecular sieve or a germanosilicate.

DETAILED DESCRIPTION OF THE INVENTION

The present invention comprises a family of molecular sieves designated herein "molecular sieve SSZ-71" or simply "SSZ-71". In preparing SSZ-71, a N-benzyl-1,4-diazabicyclo[2.2.2]octane cation (referred to herein as "benzyl DABCO") is used as a structure directing agent ("SDA"), also known as a crystallization template. The SDA useful for making SSZ-71 has the following structure:

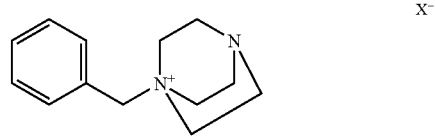

The SDA cation is associated with an anion (X⁻) which may be any anion that is not detrimental to the formation of the molecular sieve. Representative anions include halogen, e.g., fluoride, chloride, bromide and iodide, hydroxide, acetate, sulfate, tetrafluoroborate, carboxylate, and the like. Hydroxide is the most preferred anion.

Benzyl DABCO and a method for making it are disclosed in U.S. Pat. No. 5,653,956, issued Aug. 5, 1997 to Zones.

SSZ-71 is prepared from a reaction mixture having the composition shown in Table A below.

TABLE A

| | Reaction Mixture | |
|---|---|---|
| | Typical | Preferred |
| $YO_2/WO_d$ | >15 | >30 |
| $OH^-/YO_2$ | 0.10–0.50 | 0.20–0.30 |
| $Q/YO_2$ | 0.05–0.50 | 0.10–0.20 |
| $M_{2/n}/YO_2$ | 0–0.40 | 0.10–0.25 |
| $H_2O/YO_2$ | 10–80 | 15–45 | where Y is silicon, germanium or a mixture thereof; W is zinc, titanium or mixtures thereof; d is 1 or 2 (i.e., d is 1 when W is divalent or 2 when W is tetravalent); M is an alkali metal cation, alkaline earth metal cation or mixtures thereof; n is the valence of M (i.e., 1 or 2); and Q is a N-benzyl-1,4-diazabicyclo[2.2.2]octane cation.

In practice, SSZ-71 is prepared by a process comprising:

(a) preparing an aqueous solution containing sources of at least one oxide capable of forming a molecular sieve and a benzyl DABCO cation having an anionic counterion which is not detrimental to the formation of SSZ-71;

(b) maintaining the aqueous solution under conditions sufficient to form SSZ-71; and (c) recovering the SSZ-71.

SSZ-71 can be prepared as a zincosilicate or titanosilicate. However, once the SSZ-71 is made, the zinc and/or titanium can be replaced with other metals by techniques well known in the art. Accordingly, SSZ-71 may comprise the molecular sieve and the SDA in combination with metallic and non-metallic oxides bonded in tetrahedral coordination through shared oxygen atoms to form a cross-linked three dimensional crystal structure. The metallic and non-metallic oxides comprise one or a combination of oxides of (1) a first tetravalent element(s), and (2) one or a combination of a divalent element(s), trivalent element(s), pentavalent element(s), second tetravalent element(s) different from the first tetravalent element(s) or mixture thereof. The first tetravalent element(s) is preferably selected from the group consisting of silicon, germanium and combinations thereof. More preferably, the first tetravalent element is silicon. The divalent element, trivalent element, pentavalent element and second tetravalent element (which is different from the first tetravalent element) is preferably selected from the group consisting of zinc, aluminum, gallium, iron, boron, titanium, indium, vanadium and combinations thereof. More preferably, the divalent or trivalent element or second tetravalent element is zinc, aluminum, titanium or boron.

Silicon can be added as silicon oxide or $Si(OC_2H_5)_4$. Zinc can be added as a zinc salt such as zinc acetate. Titanium can be added as $Ti(OC_2H_5)_4$.

A source zeolite reagent may provide a source of metals. In most cases, the source zeolite also provides a source of silica. The source zeolite may also be used as a source of silica, with additional silicon added using, for example, the conventional sources listed above. Use of a source zeolite reagent is described in U.S. Pat. No. 5,225,179, issued Jul. 6, 1993 to Nakagawa entitled "Method of Making Molecular Sieves", the disclosure of which is incorporated herein by reference.

Typically, an alkali metal hydroxide and/or an alkaline earth metal hydroxide, such as the hydroxide of sodium, potassium, lithium, cesium, rubidium, calcium, strontium, barium and magnesium, is used in the reaction mixture; however, this component can be omitted so long as the equivalent basicity is maintained. The SDA may be used to provide hydroxide ion. Thus, it may be beneficial to ion exchange, for example, the halide to hydroxide ion, thereby reducing or eliminating the alkali metal hydroxide quantity required. The alkali metal cation or alkaline earth cation may be part of the as-synthesized material, in order to balance valence electron charges therein.

The reaction mixture is maintained at an elevated temperature until the crystals of the SSZ-71 are formed. The hydrothermal crystallization is usually conducted under autogenous pressure, at a temperature between 100° C. and 200° C., preferably between 135° C. and 160° C. The crystallization period is typically greater than 1 day and preferably from about 3 days to about 20 days.

Optionally, the molecular sieve is prepared using mild stirring or agitation.

During the hydrothermal crystallization step, the SSZ-71 crystals can be allowed to nucleate spontaneously from the reaction mixture. The use of SSZ-71 or SSZ-42 (disclosed in U.S. Pat. No. 5,653,956, issued Aug. 5, 1997 to Zones) crystals as seed material can be advantageous in decreasing the time necessary for complete crystallization to occur. In addition, seeding can lead to an increased purity of the product obtained by promoting the nucleation and/or formation of SSZ-71 over any undesired phases. When used as seeds, as-synthesized SSZ-71 or SSZ-42 crystals (containing the SDA) are added in an amount between 0.1 and 10% of the weight of first tetravalent element oxide, e.g. silica, used in the reaction mixture.

Once the molecular sieve crystals have formed, the solid product is separated from the reaction mixture by standard mechanical separation techniques such as filtration. The crystals are water-washed and then dried, e.g., at 90° C. to 150° C. for from 8 to 24 hours, to obtain the as-synthesized SSZ-71 crystals. The drying step can be performed at atmospheric pressure or under vacuum.

SSZ-71 as prepared has a mole ratio of an oxide selected from silicon oxide, germanium oxide and mixtures thereof to an oxide selected from zinc oxide, titanium oxide and mixtures thereof greater than about 15. SSZ-71 further has a composition, as synthesized (i.e., prior to calcination of the SSZ-71) and in the anhydrous state, in terms of mole ratios, shown in Table B below.

TABLE B

| As-Synthesized SSZ-71 | |
|---|---|
| $YO_2/WO_d$ | >15 |
| $M_{2/n}/YO_2$ | 0–0.03 |
| $Q/YO_2$ | 0.02–0.05 | where Y, W, d, M, n and Q are as defined above.

SSZ-71 can be made with a mole ratio of $YO_2/WO_d$ of ∞, i.e., there is essentially no $WO_d$ present in the SSZ-71. In this case, the SSZ-71 would be an all-silica material or a germanosilicate. If SSZ-71 is prepared as a zincosilicate, the zinc can be removed and replaced with metal atoms by techniques known in the art. See, for example, U.S. Pat. No. 6,117,411, issued Sep. 12, 2000 to Takewaki et al. Metals such as aluminum, gallium, iron, boron, titanium, indium, vanadium and mixtures thereof may be added in this manner.

It is believed that SSZ-71 is comprised of a new framework structure or topology which is characterized by its X-ray diffraction pattern. SSZ-71, as-synthesized, has a structure whose X-ray powder diffraction pattern exhibit the characteristic lines shown in Table I and Table II and is thereby distinguished from other molecular sieves. The XRD data shown in Table I and IA was obtained from a sample of SSZ-71 prepared in the presence of sodium hydroxide. The XRD data shown in Table II and IIA was obtained from a sample of SSZ-71 prepared in the presence of strontium hydroxide.

TABLE I

As-Synthesized Zn-SSZ-71 Prepared with NaOH

| 2 Theta[a] | d-spacing (Angstroms) | Relative Intensity[b] |
|---|---|---|
| 5.64 | 15.7 | S |
| 8.65 | 10.2 | S |
| 13.65 | 6.49 | M |
| 17.06 | 5.20 | M |
| 20.32 | 4.37 | M |
| 20.64 | 4.30 | VS |
| 23.12 | 3.85 | M |
| 24.08 | 3.70 | VS |
| 26.15 | 3.41 | M |
| 26.57 | 3.35 | M |

[a] ± 0.15
[b] The X-ray patterns provided are based on a relative intensity scale in which the strongest line in the X-ray pattern is assigned a value of 100: W(weak) is less than 20; M(medium) is between 20 and 40; S(strong) is between 40 and 60; VS(very strong) is greater than 60.

Table IA below shows the X-ray powder diffraction lines for as-synthesized Zn-SSZ-71 prepared with NaOH including actual relative intensities.

TABLE IA

| 2 Theta[a] | d-spacing (Angstroms) | Relative Intensity (%) |
|---|---|---|
| 5.64 | 15.7 | 60 |
| 8.65 | 10.2 | 57 |
| 11.40 | 7.8 | 5 |
| 11.95 | 7.4 | 7 |
| 13.11 | 6.75 | 7 |
| 13.65 | 6.49 | 21 |
| 14.34 | 6.18 | 5 |
| 17.06 | 5.20 | 29 |
| 17.84 | 4.97 | 4 |
| 18.23 | 4.87 | 10 |
| 18.84 | 4.71 | 12 |
| 19.49 | 4.55 | 18 |
| 20.32 | 4.37 | 37 |
| 20.64 | 4.30 | 100 |
| 21.55 | 4.12 | 16 |
| 22.03 | 4.03 | 16 |
| 23.12 | 3.85 | 34 |
| 24.08 | 3.70 | 62 |
| 25.29 | 3.52 | 20 |
| 25.52 | 3.49 | 20 |
| 26.15 | 3.41 | 29 |
| 26.57 | 3.35 | 33 |
| 27.15 | 3.28 | 9 |
| 28.55 | 3.13 | 18 |
| 30.00 | 2.98 | 8 |
| 30.80 | 2.90 | 5 |
| 31.68 | 2.82 | 10 |
| 32.45 | 2.76 | 5 |
| 33.16 | 2.70 | 7 |
| 34.92 | 2.57 | 11 |
| 35.61 | 2.52 | 14 |
| 36.90 | 2.44 | 12 |
| 38.82 | 2.32 | 14 |
| 40.26 | 2.24 | 12 |

[a] ± 0.15

TABLE II

As-Synthesized Zn-SSZ-71 prepared with Sr(OH)$_2$

| 2 Theta[a] | d-spacing (Angstroms) | Relative Intensity[b] |
|---|---|---|
| 5.65 | 15.6 | VS |
| 8.69 | 10.2 | VS |
| 16.99 | 5.22 | S |
| 19.52 | 4.55 | M |
| 20.60 | 4.31 | VS |
| 23.13 | 3.85 | M |
| 24.01 | 3.71 | S |
| 24.23 | 3.67 | M |
| 26.14 | 3.41 | M |
| 26.52 | 3.36 | M |

[a] ± 0.15
[b] The X-ray patterns provided are based on a relative intensity scale in which the strongest line in the X-ray pattern is assigned a value of 100: W(weak) is less than 20; M(medium) is between 20 and 40; S(strong) is between 40 and 60; VS(very strong) is greater than 60.

Table IIA below shows the X-ray powder diffraction lines for as-synthesized SSZ-71 (Zn-SSZ-71 prepared with Sr(OH)$_2$) including actual relative intensities.

TABLE IIA

| 2 Theta[a] | d-spacing (Angstroms) | Relative Intensity (%) |
|---|---|---|
| 5.65 | 15.6 | 84 |
| 8.69 | 10.2 | 67 |
| 11.36 | 7.8 | 5 |
| 11.94 | 7.4 | 5 |
| 13.17 | 6.7 | 7 |
| 13.68 | 6.5 | 20 |
| 14.34 | 6.18 | 6 |
| 15.31 | 5.79 | 2 |
| 16.99 | 5.22 | 42 |
| 18.24 | 4.86 | 8 |
| 18.79 | 4.72 | 17 |
| 19.52 | 4.55 | 26 |
| 20.34 | 4.37 | 23 |
| 20.60 | 4.31 | 100 |
| 21.59 | 4.12 | 13 |
| 22.06 | 4.03 | 16 |
| 23.13 | 3.85 | 37 |
| 24.01 | 3.71 | 41 |
| 24.23 | 3.67 | 25 |
| 25.25 | 3.53 | 20 |
| 25.52 | 3.49 | 23 |
| 26.14 | 3.41 | 36 |
| 26.52 | 3.36 | 30 |
| 27.10 | 3.29 | 12 |
| 28.52 | 3.13 | 22 |
| 29.85 | 2.99 | 6 |
| 30.24 | 2.96 | 2 |
| 30.84 | 2.90 | 3 |
| 31.64 | 2.83 | 11 |
| 32.44 | 2.76 | 5 |
| 33.11 | 2.71 | 5 |
| 34.86 | 2.57 | 6 |
| 35.63 | 2.52 | 14 |
| 36.10 | 2.49 | 6 |

[a] ± 0.15

The X-ray powder diffraction patterns were determined by standard techniques. The radiation was the K-alpha/doublet of copper. The peak heights and the positions, as a function of 2θ where θ is the Bragg angle, were read from the relative intensities of the peaks, and d, the interplanar spacing in Angstroms corresponding to the recorded lines, can be calculated.

The variation in the scattering angle (two theta) measurements, due to instrument error and to differences between individual samples, is estimated at ±0.15 degrees.

The X-ray diffraction pattern of Table I is representative of "as-synthesized" or "as-made" SSZ-71 molecular sieves. Minor variations in the diffraction pattern can result from variations in the silica-to-zinc or silica-to-titanium mole ratio of the particular sample due to changes in lattice constants. In addition, sufficiently small crystals will affect the shape and intensity of peaks, leading to significant peak broadening.

The molecular sieve produced by exchanging the metal or other cations present in the molecular sieve with various other cations (such as $H^+$ or $NH_4^+$) yields essentially the same diffraction pattern, although again, there may be minor shifts in the interplanar spacing and variations in the relative intensities of the peaks. Notwithstanding these minor perturbations, the basic crystal lattice remains unchanged by these treatments.

SSZ-71 can be used as-synthesized, but preferably will be thermally treated (calcined). Usually, it is desirable to remove the alkali metal cation by ion exchange and replace it with hydrogen, ammonium, or any desired metal ion. The molecular sieve can also be steamed; steaming helps stabilize the molecular sieve to attack from acids.

The molecular sieve can be used in intimate combination with hydrogenating components, such as tungsten, vanadium, molybdenum, rhenium, nickel, cobalt, chromium, manganese, or a noble metal, such as palladium or platinum, for those applications in which a hydrogenation-dehydrogenation function is desired.

Metals may also be introduced into the molecular sieve by replacing some of the cations in the molecular sieve with metal cations via standard ion exchange techniques (see, for example, U.S. Pat. No. 3,140,249 issued Jul. 7, 1964 to Plank et al.; U.S. Pat. No. 3,140,251 issued Jul. 7, 1964 to Plank et al.; and U.S. Pat. No. 3,140,253 issued Jul. 7, 1964 to Plank et al.). Typical replacing cations can include metal cations, e.g., rare earth, Group IA, Group IIA and Group VIII metals, as well as their mixtures. Of the replacing metallic cations, cations of metals such as rare earth, Mn, Ca, Mg, Zn, Cd, Pt, Pd, Ni, Co, Ti, Al, Sn, and Fe are particularly preferred.

The hydrogen, ammonium, and metal components can be ion-exchanged into the SSZ-71. The SSZ-71 can also be impregnated with the metals, or the metals can be physically and intimately admixed with the SSZ-71 using standard methods known to the art.

Typical ion-exchange techniques involve contacting the synthetic molecular sieve with a solution containing a salt of the desired replacing cation or cations. Although a wide variety of salts can be employed, chlorides and other halides, acetates, nitrates, and sulfates are particularly preferred. The molecular sieve is usually calcined prior to the ion-exchange procedure to remove the organic matter present in the channels and on the surface, since this results in a more effective ion exchange. Representative ion exchange techniques are disclosed in a wide variety of patents including U.S. Pat. No. 3,140,249 issued on Jul. 7, 1964 to Plank et al.; U.S. Pat. No. 3,140,251 issued on Jul. 7, 1964 to Plank et al.; and U.S. Pat. No. 3,140,253 issued on Jul. 7, 1964 to Plank et al.

Following contact with the salt solution of the desired replacing cation, the molecular sieve is typically washed with water and dried at temperatures ranging from 65° C. to about 200° C. After washing, the molecular sieve can be calcined in air or inert gas at temperatures ranging from about 200° C. to about 800° C. for periods of time ranging from 1 to 48 hours, or more, to produce a catalytically active product especially useful in hydrocarbon conversion processes.

Regardless of the cations present in the synthesized form of SSZ-71, the spatial arrangement of the atoms which form the basic crystal lattice of the molecular sieve remains essentially unchanged.

SSZ-71 can be formed into a wide variety of physical shapes. Generally speaking, the molecular sieve can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the SSZ-71 can be extruded before drying, or, dried or partially dried and then extruded.

SSZ-71 can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and U.S. Pat. No. 5,316,753, issued May 31, 1994 to Nakagawa, both of which are incorporated by reference herein in their entirety.

The molecular sieve of the present invention can be used in a catalyst for acylating an aromatic substrate $ArH_n$, where n is at least 1, by reacting the aromatic substrate with an acylating agent in the presence of the catalyst. The product of the acylation reaction is $ArH_{n-1}COR$ where R is an organic radical.

Examples of the aromatic substrate include, but are not limited to, benzene, toluene, anisole and 2-naphthol. Examples of the acylating agent included, but are not limited to, carboxylic acid derivatives, carboxylic acids, acid anhydrides, esters, and acyl halides.

Reaction conditions are known in the art (see, for example, U.S. Pat. No. 6,630,606, issued Oct. 7, 2003 to Poliakoff et al., U.S. Pat. No. 6,459,000, issued Oct. 1, 2002 to Choudhary et al., and U.S. Pat. No. 6,548,722, issued Apr. 15, 2003 to Choudhary et al., all of which are incorporated herein by reference in their entirety). Typically, the acylation reaction is conducted with a weight ratio of the catalyst to the acylating agent of about 0.03 to about 0.5, a mole ratio of aromatic substrate to acylating agent of about 1.0 to about 20, a reaction temperature in the range of about 20° C. to about 200° C., a reaction pressure in the range of about 1 atm to about 5 atm, and a reaction time of about 0.05 hours to about 20 hours.

EXAMPLES

The following examples demonstrate but do not limit the present invention.

Examples 1A–1H

Synthesis of Zincosilicate SSZ-71 (Zn-SSZ-71)

Zn-SSZ-71 is synthesized by preparing the gels, i.e., reaction mixtures, having the compositions, in terms of mole ratios, shown in the table below. 9.06 g of benzyl DABCO hydroxide (0.815 mmol/g) solution are mixed with 13.8 g of deionized water. Then, respectively, an appropriate amount of ammonium hydroxide or alkali hydroxide or alkaline earth hydroxide is added. Subsequently, 0.18 g of Zn(CH$_3$COO)$_2$ are added and stirred at room temperature overnight. Finally, 1.63 g of Cab-O-Sil M-5 are mixed and stirred at room temperature for 1 hour. The resulting gel is placed in a Parr bomb reactor and heated in an oven at 150° C. while rotating at 43 rpm. The reaction is held under these conditions for 17 and 29 days, respectively, of run time.

| Ex. No. | Gel Composition | Remark |
|---|---|---|
| 1A | 0.018 (NH$_4$)$_2$:0.15 R$_2$O: 0.03 Zn(CH$_3$COO)$_2$:SiO$_2$:43 H$_2$O | with NH$_4$OH only without AlkOH or AlkE(OH)$_2$ |
| 1B–1F | 0.018 Alk$_2$O:0.15 R$_2$O: 0.03 Zn(CH$_3$COO)$_2$:SiO$_2$:43 H$_2$O | Alk = Li, Na, K, Rb or Cs (all in hydroxide form) |
| 1G–1H | 0.018 AlkEO:0.15 R$_2$O: 0.03 Zn(CH$_3$COO)$_2$:SiO$_2$:43 H$_2$O | AlkE = Sr or Ba (all in hydroxide form) |

R is benzyl DABCO in hydroxide form.
Alk is alkali metal.
AlkE is alkaline earth metal.

The products are analyzed by X-ray diffraction and determined to be Zn-SSZ-71.

Examples 2A–2D

Synthesis of Zincosilicate SSZ-71 (Zn-SSZ-71)

Zn-SSZ-71 is synthesized using the procedure of Examples 1A–1H except that EDTA (ethylenediaminetetraacetic acid) is added together with NaOH to the benzyl DABCO hydroxide solution. The reaction is run at 150° C. under rotation at 43 rpm. The gel composition is given below.

| Ex. No. | Gel Composition | Synthesis Time, days |
|---|---|---|
| 2A | 0.018 Na$_2$O:0.15 R$_2$O:0.03 EDTA: 0.03 Zn(CH$_3$COO)$_2$:SiO$_2$:43 H$_2$O | 7 |
| 2B | 0.018 Na$_2$O:0.15 R$_2$O: 0.03 EDTA:0.03 Zn(CH$_3$COO)$_2$:SiO$_2$:43 H$_2$O | 15 |
| 2C | 0.018 Na$_2$O:0.15 R$_2$O: 0.03 EDTA:0.03 Zn(CH$_3$COO)$_2$:SiO$_2$:43 H$_2$O | 22 |
| 2D | 0.018 Na$_2$O:0.15 R$_2$O: 0.03 EDTA:0.03 Zn(CH$_3$COO)$_2$:SiO$_2$:43 H$_2$O | 29 |

R is benzyl DABCO in hydroxide form.

The products are analyzed by X-ray diffraction and determined to be Zn-SSZ-71.

Examples 3A–3B

Synthesis of All-Silica SSZ-71 (Si-SSZ-71) Using Boron-SSZ-42 as Seeds

Si-SSZ-71 is synthesized using the procedure of Example 1A–1H except that (1) no Zn(CH$_3$COO)$_2$ is added, (2) 2 wt. % as-made B-SSZ-42 (on the SiO$_2$ base) is used as seeds and (3) the reaction is run under static conditions. The gel compositions (excluding the seeds) are given below. The reaction is held under these conditions for 14 days of run time.

| Ex. No. | Gel Composition |
|---|---|
| 3A | 0.018 (NH$_4$)$_2$O:0.15 R$_2$O:SiO$_2$:43 H$_2$O |
| 3B | 0.018 K$_2$O:0.15 R$_2$O:SiO$_2$:43 H$_2$O |

R is benzyl DABCO in hydroxide form.

The products are analyzed by XRD and found to be Si-SSZ-71.

Examples 4A–4C

Synthesis of All-Silica SSZ-71 (Si-SSZ-71) Using Si-SSZ-71 as Seeds

Si-SSZ-71 is synthesized using the procedure of Examples 3A–3B under static conditions except that 2 wt. % as-made Si-SSZ-71 (on the SiO$_2$ base) is used as seeds and no ammonium hydroxide or alkali hydroxide such as KOH is used. The gel composition (excluding the seeds) is given below.

| Ex. No. | Gel Composition | Synthesis Time, days |
|---|---|---|
| 4A | 0.15 R$_2$O:SiO$_2$:43 H$_2$O | 2.6 |
| 4B | 0.15 R$_2$O:SiO$_2$:43 H$_2$O | 28 |
| 4C | 0.15 R$_2$O:SiO$_2$:43 H$_2$O | 38 |

R is benzyl DABCO in hydroxide form.

The products are analyzed by XRD and found to be Si-SSZ-71 (the product of Example 4A contained SSZ-42 as an impurity).

Examples 5A–5C

Synthesis of Si-SSZ-71

Si-SSZ-71 is synthesized as described in Examples 4A–4C under the following conditions:

(1) with varying amount of water but otherwise identical gel composition,
(2) without NH$_4$OH or other alkali or alkaline earth hydroxide (e.g., KOH, etc.),
(3) without seeds,
(4) under tumbling at 43 rpm,
(5) at 150° C.,
(6) with two different synthesis time: 15 and 30 days.

The gel compositions and conditions are given below:

| Ex. No. | Gel Composition | Tumbled at 43 rpm 150° C. | |
|---|---|---|---|
| 5A | (1) 0.15 R$_2$O:SiO$_2$:43 H$_2$O | 15 d | 30 d |
| 5B | (2) 0.15 R$_2$O:SiO$_2$:29 H$_2$O | 15 d | 30 d |
| 5C | (3) 0.15 R$_2$O:SiO$_2$:15 H$_2$O | 15 d | 30 d |

R is benzyl DABCO in hydroxide form.

The products are analyzed by XRD and found to be Si-SSZ-71 with the exception of Example 5C at 15 days, which remained a gel.

Examples 6A–6F

Synthesis of Titanosilicate SSZ-71 (Ti-SSZ-71)

Ti-SSZ-71 is synthesized by preparing the gels, i.e., reaction mixtures, having the composition, in terms of mole ratios, shown in the table below. $Ti(OC_2H_5)_4$ and Cab-O-Sil M-5 are used as titanium and silicon source, respectively. 126.2 g of benzyl DABCO hydroxide (0.614 mmol/g) solution are mixed with 7.3 g of deionized water. Then, 0.61 g of $Ti(OC_2H_5)_4$ are added under vigorous stirring and then further stirred at room temperature overnight. Subsequently, an appropriate amount of water is added to reach the water content given in the gel composition below because some water is evaporated when stirred overnight. Finally, 18.14 g of Cab-O-Sil M-5 are mixed and stirred at room temperature for 1 hour. The resulting gel is placed in a Parr bomb reactor and heated in an oven at 150 or 160° C. while rotating at 43 rpm.

| Ex. No. | Gel Composition | Temp, ° C. | Time, days |
|---|---|---|---|
| 6A | 0.15 $R_2O$:0.01 $Ti(OC_2H_5)_4$:$SiO_2$:25 $H_2O$ | 150 | 7 |
| 6B | 0.15 $R_2O$:0.01 $Ti(OC_2H_5)_4$:$SiO_2$:25 $H_2O$ | 150 | 14 |
| 6C | 0.15 $R_2O$:0.01 $Ti(OC_2H_5)_4$:$SiO_2$:25 $H_2O$ | 150 | 21 |
| 6D | 0.15 $R_2O$:0.01 $Ti(OC_2H_5)_4$:$SiO_2$:25 $H_2O$ | 160 | 7 |
| 6E | 0.15 $R_2O$:0.01 $Ti(OC_2H_5)_4$:$SiO_2$:25 $H_2O$ | 160 | 14 |
| 6F | 0.15 $R_2O$:0.01 $Ti(OC_2H_5)_4$:$SiO_2$:25 $H_2O$ | 160 | 21 |

R is benzyl DABCO in hydroxide form.

The products are analyzed by X-ray diffraction and determined to be Ti-SSZ-71.

Examples 7A–7F

Synthesis of Titanosilicate SSZ-71 (Ti-SSZ-71)

Ti-SSZ-71 is synthesized by preparing the gels, i.e., reaction mixtures, having the composition, in terms of mole ratios, shown in the table below. $Ti(OC_2H_5)_4$ and $Si(OC_2H_5)_4$ are used as titanium and silicon source, respectively. 39.13 g of $Si(OC_2H_5)_4$ are placed in a plastic beaker. 1.30 g of $Ti(OC_2H_5)_4$ are then quickly added to $Si(OC_2H_5)_4$ under stirring. The mixture of $Ti(OC_2H_5)_4$ and $Si(OC_2H_5)_4$ is placed in an ice bath. 107.0 g of benzyl DABCO hydroxide (0.614 mmol/g) solution are added to this mixture under vigorous stirring and then further stirred at room temperature overnight. Subsequently, an appropriate amount of water is added to reach the water content given in the gel composition below because some water is evaporated when stirred overnight. The resulting gel is placed in a Parr bomb reactor and heated in an oven at 150 or 160° C. while rotating at 43 rpm.

| Ex. No. | Gel Composition | Temp, ° C. | Time, days |
|---|---|---|---|
| 7A | 0.175 $R_2O$:0.03 $Ti(OC_2H_5)_4$:$SiO_2$:28 $H_2O$ | 160 | 7 |
| 7B | 0.175 $R_2O$:0.03 $Ti(OC_2H_5)_4$:$SiO_2$:28 $H_2O$ | 160 | 14 |
| 7C | 0.175 $R_2O$:0.03 $Ti(OC_2H_5)_4$:$SiO_2$:28 $H_2O$ | 160 | 21 |
| 7D | 0.175 $R_2O$:0.03 $Ti(OC_2H_5)_4$:$SiO_2$:28 $H_2O$ | 150 | 7 |
| 7E | 0.175 $R_2O$:0.03 $Ti(OC_2H_5)_4$:$SiO_2$:28 $H_2O$ | 150 | 14 |
| 7F | 0.175 $R_2O$:0.03 $Ti(OC_2H_5)_4$:$SiO_2$:28 $H_2O$ | 150 | 21 |

R is benzyl DABCO in hydroxide form.

The products are analyzed by X-ray diffraction and determined to be Ti-SSZ-71.

Examples 8A–8C

Synthesis of Titanosilicate SSZ-71 (Ti-SSZ-71)

Si-SSZ-71 is synthesized as described in Examples 7A–7F except that 2 wt. % as-made Si-SSZ-71 (on the $SiO_2$ base) is used as seeds. The gel composition (excluding the seeds) is given below. $Ti(OC_2H_5)_4$ and $Si(OC_2H_5)_4$ are used as titanium and silicon source, respectively. The resulting gel is placed in a Parr bomb reactor and heated in an oven at 150° C. while rotating at 43 rpm.

| Ex. No. | Gel Composition | Temp, ° C. | Time, days |
|---|---|---|---|
| 8A | 0.175 $R_2O$:0.01 $Ti(OC_2H_5)_4$:$SiO_2$:28 $H_2O$ | 150 | 6 |
| 8B | 0.175 $R_2O$:0.01 $Ti(OC_2H_5)_4$:$SiO_2$:28 $H_2O$ | 150 | 18 |
| 8C | 0.175 $R_2O$:0.01 $Ti(OC_2H_5)_4$:$SiO_2$:28 $H_2O$ | 150 | 24 |

R is benzyl DABCO in hydroxide form.

The products are analyzed by X-ray diffraction and determined to be Ti-SSZ-71.

Example 9

Calcination of Zn-SSZ-71

Na/Zn-SSZ-71 as synthesized in Example IC with NaOH is calcined to remove the structure directing agent (SDA) as described below. A thin bed of Na/Zn-SSZ-71 in a calcination dish is heated in a muffle furnace from room temperature to 120° C. at a rate of 1° C./minute and held for 2 hours. Then, the temperature is ramped up to 540° C. at a rate of 1° C./minute and held for 5 hours. The temperature is ramped up again at 1° C./minute to 595° C. and held there for 5 hours. A 50/50 mixture of air and nitrogen passes through the muffle furnace at a rate of 20 standard cubic feet (0.57 standard cubic meters) per minute during the calcination process.

Example 10

Conversion of calcined Zn-SSZ-71 to Al-SSZ-71

The calcined Na/Zn-SSZ-71 (5 g) prepared in Example 9 is with combined with 500 grams of 1 M aqueous $Al(NO_3)_3$ solution and treated under reflux for 100 hours. The resulting Al-SSZ-71 product is then washed with 1 liter of water, filtered and air-dried at room temperature in vacuum filter.

Example 11

The Al-SSZ-71 material prepared in Example 10 is loaded with 1.0 wt.-% Pt via impregnation with aqueous $Pt(NH_3)_4(NO_3)_2$ solution and tested with bifunctionally catalyzed hydrocracking of FCC LCO (light cycle oil). The FCC LCO is first hydrotreated over a Ni/Mo hydrotreating catalyst at 660° F. and 1700 psig to reduce its sulfur and nitrogen contents. The hydrotreated LCO is then hydrocracked over Pt/Al-SSZ-71 at 750° F. and 1000 psig. The results from the simulated distillation via GC analysis are given below.

| | Temperature, ° F. | | |
|---|---|---|---|
| Volume Percent Intervals, % | Untreated LCO | Hydrotreated LCO over Ni/Mo catalyst | Hydrocracked LCO over Pt/Al-SSZ-71 |
| 5 | 393 | 382 | 273 |
| 10 | 436 | 417 | 322 |
| 15 | 453 | 437 | 366 |
| 20 | 477 | 455 | 395 |
| 25 | 491 | 467 | 413 |
| 30 | 502 | 481 | 433 |
| 35 | 520 | 495 | 445 |
| 40 | 534 | 508 | 457 |
| 45 | 546 | 522 | 471 |
| 50 | 562 | 535 | 484 |
| 55 | 577 | 548 | 497 |
| 60 | 593 | 563 | 513 |
| 65 | 609 | 576 | 529 |
| 70 | 623 | 592 | 542 |
| 75 | 637 | 608 | 560 |
| 80 | 652 | 625 | 576 |
| 85 | 670 | 643 | 599 |
| 90 | 689 | 666 | 623 |
| 95 | 716 | 699 | 660 |

What is claimed is:

1. A method for performing an acylation reaction on an aromatic substrate $ArH_n$ to form a product $ArH_{n-1}COR$, the method comprising the steps of:

providing the aromatic substrate, intimately mixing the substrate and an acylating agent, wherein the acylating agent is selected from the group consisting of a carboxylic acid derivative, a carboxylic acid, an acid anhydride, an ester, and an acyl halide, and exposing an intimate mixture thus formed to a catalyst comprising a molecular sieve produced by the method comprising:

(1) preparing an as-synthesized molecular sieve having a composition, as synthesized and in the anhydrous state, in terms of mole ratios as follows:

$YO_2/WO_d$ 15–∞

$M_{2/n}/YO_2$ 0–0.03

$Q/YO_2$ 0.02–0.05 wherein Y is silicon, germanium or a mixture thereof; W is zinc, titanium or mixtures thereof; d is 1 or 2 (i.e., d is 1 when W is divalent or 2 when W is tetravalent); M is an alkali metal cation, alkaline earth metal cation or mixtures thereof; n is the valence of M (i.e., 1 or 2); and Q is a N-benzyl-1,4-diazabicyclo[2.2.2]octane cation, the as-synthesized molecular sieve having the X-ray diffraction lines of Table I;

(2) thermally treating the as-synthesized molecular sieve at a temperature and for a time sufficient to remove the N-benzyl-1,4-diazabicyclo[2.2.2]octane cation from the molecular sieve; and (3) optionally, replacing at least part of the zinc and/or titanium with a metal selected from the group consisting of aluminum, gallium, iron, boron, indium, vanadium and mixtures thereof.

2. The method of claim 1 wherein the organic substrate is selected from the group consisting of benzene, toluene, anisole and 2-naphthol.

3. The method of claim 2 wherein the organic substrate is anisole.

4. The method of claim 1 wherein the acylating agent is selected from the group consisting of carboxylic acid derivatives, carboxylic acids, acid anhydrides, esters, and acyl halides.

* * * * *